US00PP12138P2

(12) United States Plant Patent
Heims

(10) Patent No.: US PP12,138 P2
(45) Date of Patent: Oct. 9, 2001

(54) PULMONARIA PLANT NAMED 'RASPBERRY SPLASH'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/324,623

(22) Filed: Jun. 2, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Klarquist Sparkman Campbell Leigh & Whinston LLP

(57) ABSTRACT

A new and distinct hybrid of Pulmonaria characterized by large bright raspberry-colored flowers with upright, well marked foliage and an extended bloom period.

1 Drawing Sheet

The present invention relates to a new and distinct cultivated variety of Pulmonaria which originated as a hybrid between *Pulmonaria longifolia* 'Bertram Anderson', unpatented (pod parent), and Pulmonaria 'Leopard', unpatented (pollen parent of hybrid origin). Neither parent is patented or protected in the U.S.

The new Pulmonaria is a result of a controlled cross of the aforementioned plants in Canby, Oreg. This hybrid was selected from a large number of seedlings. Parent plants were retained to observe habit and to compare with the new variety. The new variety has been reproduced only by asexual propagation (division and tissue culture). Each of the progeny exhibits identical characteristics to the original as evidenced by the following characteristics: large flowers (compared to other *Pulmonaria longifolia* hybrids in the marketplace), sharply tipped foliage, and intense flower color.

Asexual propagation by division and tissue cultures done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRPAH

The FIGURE shows flowers and foliage in April in Canby, Oreg.

DETAILED PLANT DESCRIPTION

The following is a detailed description of the new Pulmonaria hybrid based on observations of 1.5–2-year-old field-grown specimens in Canby, Oreg. The color descriptions are all based on the The Royal Horticultural Society Color Chart.

Size of a 2-year-old plant grown in soil in Canby, Oreg.:
*Height.*—to 30 cm.
*Width.*—to 65 cm.
Habit: Mounding.
Foliage:
*Basal.*—Type — Simple; Herbaceous (evergreen in USDA hardiness Zones 6 to 9, herbaceous in USDA hardiness zone 4 and 5.) Shape — Lanceolate.

Length — 18–24 cm. Width — 5.5–7.5 cm. Petiole Length — 8–10 cm. Apex — Acuminate to narrowly-acute. Margins — Cilate, entire. Base — Attenuate. Texture — Uniform bristle-like pubescence on both upper and lower surfaces. Leaf Arrangement — Basal clump. Venation — Reticulate-pinnate. Appearance — Spotted.
*Cauline* (*observed on inflorescence only and does not persist after inflorescence senesces; unless stated below, other foliage characteristics are the same as for basal leaves*).—Leaf Arrangement — Opposite. Base — Sessile. Length — to 7 cm. Width — 1.5–2 cm.
Flower:
*Flower type.*—Complete, perfect.
*Reproductive organs.*—Stamens: Included. Anther number: 5. Pistil: Exserted (pin-type). Ovary position: Partly inferior. Placentation: One-chambered, basal.
*Flowers.*—Diameter: 0.75–1.2 cm from petal tip to petal tip. Length: 1 cm. Corolla shape: Funnelform. Petal length: 0.4 cm. Petal width: 0.35 cm. Petal number: 5. Petal texture: smooth, undulate. Base is fused. Petal color: Color ranges from RHS Red Purple Group 67A to RHS Red Purple Group 67C. Same color inside and out of the corolla except for a more intense ring at the outside corolla base. Ring color is RHS Red Purple Group 74B. Calyx shape: Urceolate, fused. Calyx color: RHS 138A Green Group. Calyx length: 1 cm. Calyx width: 0.35 cm. Calyx texture: calyx has a uniform bristle-like pubescence. Sepal number: 5. Fragrance: None.
*Blooming habit.*—Bracted, terminal forked cymes, 15–20 flowers per cyme, 50–75 cymes on a two-year plant.
*Peduncle length.*—to 19 cm.
*Peduncle width.*—4 mm tapering to 1.5 mm at pedicels.
*Peduncle texture.*—Bristle-like pubescence.
*Bloom period.*—Third week in February to first week in May in Canby, Oreg.
*Lastingness of bloom.*—Blooms will hold color for 7 days if not pollinated. If pollinated, blooms will drop in 4 days.
Fruit: 4 smooth nutlets.
Disease: Minor susceptibility to powdery mildew has been observed on plants grown commercially in Canby, Oreg.

Color characteristics:

*Foliage.*—Mature leaves, upper surface, background RHS Yellow Green Group 147A; mature leaves, upper surface, spotted areas, RHS Greyed Green Group 191A; mature leaves lower surface, RHS green Group 138A.

*Flowers.*—Color ranges from RHS Red Purple Group 67A to RHS Red Purple Group 67C; same color inside and outside of petals, except for a more intense ring at the outside corolla base- Ring color is RHS Red Purple Group 74B; calyx color is RHS Green Group 138A.

*Peduncle.*—R.H.S. Yellow-Green Group 148C.

DESCRIPTION OF PARENT PLANTS

*Pulmonaria longifolia* 'Bertram Anderson' (pod parent) has small, cobalt-blue flowers, typical of *Pulmonaria longifolia*, and Pulmonaria 'Leopard' (pollen parent of hybrid origin) has large, widely splayed flowers with a similar range of color as Pulmonaria "Raspberry Splash". Pulmonaria 'Leopard' has a much lower growth habit, similar to *Pulmonaria saccharata*. Pulmonaria 'Raspberrry Splash' has characteristics which make it unique from its parents, having raspberry colored flowers of the *Pulmonaria longifolia*-type (small, narrowly splayed blooms), with narrow, upright, silver-splashed foliage.

I claim:

1. A new and distinct hybrid of Pulmonaria substantially as shown and described, characterized by large bright rapsberry-colored flowers with upright, well marked foliage and an extended bloom period.

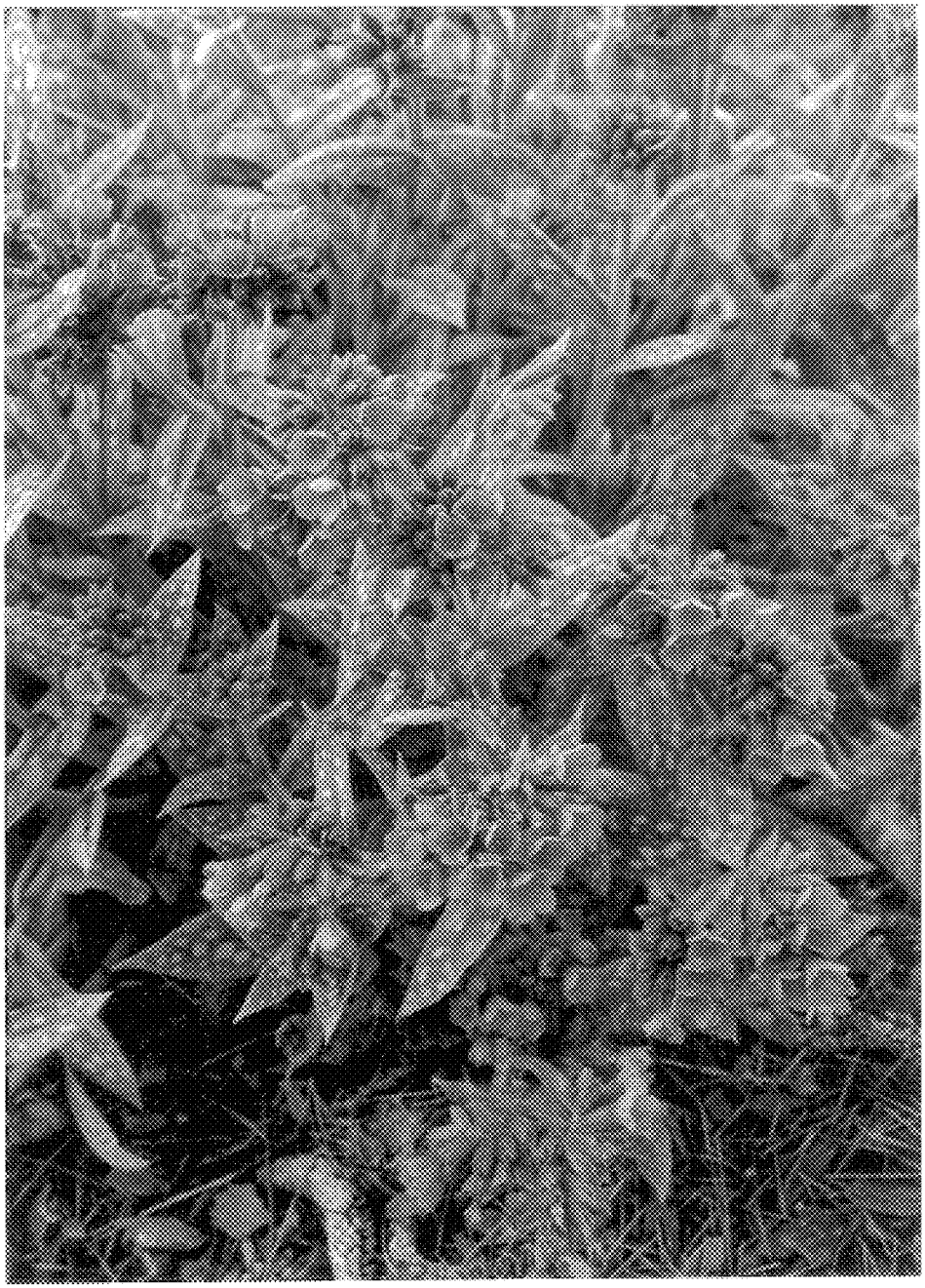

* * * * *